United States Patent
Scharlemann

(10) Patent No.: US 6,617,849 B1
(45) Date of Patent: Sep. 9, 2003

(54) DEVICE FOR THE NONDESTRUCTIVE TESTING OF ESPECIALLY HOT BAR SHAPED ROLLING MATERIAL

(75) Inventor: Horst Scharlemann, deceased, late of Hagen (DE), by Brigitte Scharlemann, legal heir

(73) Assignee: Georgsmarienhütte GmbH, Georgsmarienhütte (DE)

( * ) Notice: Subject to any disclaimer, the term of this patent is extended or adjusted under 35 U.S.C. 154(b) by 0 days.

(21) Appl. No.: 09/762,576
(22) PCT Filed: Jun. 14, 2000
(86) PCT No.: PCT/DE00/01971
§ 371 (c)(1),
(2), (4) Date: Nov. 26, 2001
(87) PCT Pub. No.: WO00/77513
PCT Pub. Date: Dec. 21, 2000

(30) Foreign Application Priority Data

Jun. 15, 1999 (DE) .......................................... 199 27 061

(51) Int. Cl.$^7$ .............................................. G01N 27/82
(52) U.S. Cl. ........................ 324/224; 324/238; 324/262
(58) Field of Search ................................ 324/225, 224, 324/239, 240, 242, 262, 238; 336/57, 58

(56) References Cited

U.S. PATENT DOCUMENTS

| 2,020,067 A | * | 11/1935 | Keinath ...................... 374/184 |
|---|---|---|---|
| 3,424,976 A | * | 1/1969 | Jezewski et al. ............ 324/225 |
| 4,024,470 A | | 5/1977 | Vild et al. .................. 324/224 |
| 4,461,995 A | | 7/1984 | Harris ........................ 324/224 |
| 4,534,405 A | * | 8/1985 | Hulek et al. ................ 164/451 |
| 4,596,953 A | * | 6/1986 | Nagasaka et al. ........... 324/242 |
| 4,644,274 A | * | 2/1987 | Casarcia ..................... 324/262 |
| 5,187,435 A | * | 2/1993 | Geweke ...................... 324/225 |
| 5,550,468 A | * | 8/1996 | Haberlein et al. .......... 324/225 |
| 6,014,024 A | * | 1/2000 | Hockey et al. ............. 324/240 |

FOREIGN PATENT DOCUMENTS

GB  2 014 317  8/1979

* cited by examiner

Primary Examiner—N. Le
Assistant Examiner—Reena Aurora
(74) Attorney, Agent, or Firm—Collard & Roe, P.C.

(57) ABSTRACT

A device for nondestructive testing of especially hot, bar-shaped rolling material above Curie point during the rolling process by means of an exploring coil system which can be impinged upon by a coolant and which rotates around the rolling material passing therethrough. The exploring coil system consists of at least two exploring coils. The invention is characterized in that the inventive device is arranged directly downstream from the point where the rolled product exits from the roll stand on the roller cooling system associated therewith. The invention is further characterized in that the coolant for the explorer coil system is fed into the rotating system essentially on the same plane as the one on which the device is secured to the roll stand, wherein a channel for said coolant is provided, extending in a threaded manner between the rolled product and the rotation bearing and wherefrom individual ducts lead to the respective explorer coils in a radial manner.

6 Claims, 3 Drawing Sheets

DEVICE FOR THE NONDESTRUCTIVE TESTING OF ESPECIALLY HOT BAR SHAPED ROLLING MATERIAL

The invention relates to a device for testing in a nondestructive manner in the course of the rolling process particularly hot, rod-shaped rolling stock above the Curie point, by means of a test coil system that rotates around the rolling stock passing through and which can be acted upon by a coolant, said test coil system consisting of at least two test coils.

Such devices are known per se, for example from GB-A-2 014 317. Said document shows (particularly in FIG. 2) a rotating test coil system that can be driven on rails to the test location, the latter being limited by the course of the rails. Said known device is conspicuous primarily on account of its long type of construction, which, in addition to the drawback that said it cannot be employed in any desired location, has the further disadvantages that exactly straight guidance of the material to be tested cannot be assured; that measurement errors may occur, on the one hand, and that the device may be damaged or even destroyed on the other.

Because of the length of the device, furthermore, feeding of the water for cooling and flushing both the coil and the rotating bearings is complicated and requires substantial expenditure.

Therefore, the invention is based on the problem of realizing a device of the type specified above in such a way that it can be installed in the form of a small structure in any desired location in the rolling mill where exact straight guidance of the rolling stock is naturally assured.

Said problem is solved by the invention according to the characterizing part of claim 1 in that the device is arranged directly downstream of the point where the rolled material exits from the rolling stand, specifically on the roll cooling system associated with said rolling stand; and in that the coolant for the test coil system is fed into the rotating system approximately in the plane in which the device is secured on the rolling stand. In said rotating system, provision is made for a coolant channel extending in the manner of a thread between the rolled material and the rotational bearing up to its face side, with individual ducts leading to the respective test coils in a radial manner.

Such an arrangement is particularly suitable in conjunction with so-called multi-roll rolling stands, where provision is made, for example for three rolls or rollers each being arranged offset by 120° in relation to each other (a so-called Kocks block), and where in such a block a first roll triple is followed at a distance of about 35 cm by another roll triple. The device as defined by the invention is designed in such a way that it fits between the roll triples in said relatively confined space. Owing to the fact that the two roll triples follow each other so closely, exactly straight guidance of the rolling stock is assured, so that no further adjustment work is required after the device as defined by the invention has been set up and first adjustments have been made.

Furthermore, arranging the device as defined by the invention in the location (roll cooling system) specified in the characterizing part of claim 1 offers the further advantage that the cooling medium required for cooling the test coils is directly available in said location, and that said coolant, furthermore, can be directly fed there into the rotating part of the device within the zone where the device is secured. From there, the coolant can be passed through the channel extending in the manner of a thread, and guided to the individual test coils via the ducts branching off from said channel in a radial manner.

The thread-like channel is produced by cutting a thread-like groove into the surface of a cylinder belonging to the rotating part of the device. Said groove is covered by a second cylinder, which is pushed over the first cylinder.

The thread-like course of the coolant duct results in a large heat-absorbing surface that is located between the rolling stock and the rotating bearing and the signal transmitters, which are located in the rotating part of the device, on the one hand, and in the stationary part on the other. Said signal transmitters are connected to the test coils.

Especially in conjunction with the type of three-roll rolling stands described above, arranging the device as defined by the invention on the roll cooling system is suitable because the roll cooling system consists there of a channel surrounding the outlet for the rolled material in the form of a ring, whereby nozzle lines leading to the surfaces of the rolls are branching off from said channel in a radial manner. The stationary part of the device as defined by the invention is flanged to the housing surrounding the ring-shaped channel.

A particularly preferred embodiment of the test coils in the device as defined by the invention is specified in claim 3. In said embodiment, the test coils each are arranged on an approximately L-shaped support, specifically on the end of the longer leg of the "L", and the support can be pivoted around an axle extending in the zone of the point of intersection of the legs. The supports, therefore, form angle levers.

Said design of the supports in the form of angle levers results in a point-symmetrical arrangement around the axis of the device. However, the important advantage offered by said design has to be seen in the swinging capability of the supports, by virtue of which it is possible to change the spacing of the individual test coils from the rolled stock to be tested.

The essential feature of the invention ensues in conjunction with the swinging capability of the supports of the test coils. Said feature is provided by claims 4 and 5 and specifies that the defined measuring position of the test coils is automatically assumed by said test coils only once defined parameters have been satisfied.

According to the features of claim 4, one of the legs of the L-shaped support is engaged by a spring that retains the test coil in a position that is removed from the rolled stock until a defined rotation frequency is exceeded, whereupon the test coil is driven into the measuring position as a result of increased centrifugal force.

Such a spring engages, for example the shorter leg of the "L" which has a counterweight making said leg heavier than the longer leg of the "L". The spring ensures that the longer leg of the "L" with the test coil arranged thereon remains swung out of the measuring position until an adequate rotational speed of the test coil system has been reached. Said rotational speed is attained only if the leading end of the rolling stock to be measured (which naturally contains many impurities and errors and is later cut off, and which, furthermore, does not have the absolute straightness required for the measurement) has passed the measuring site. The frequency of rotation of the test coil system is adequately high for overcoming the force of the spring only then, and the shorter leg is then driven outwards due to the centrifugal force, which drives the test coil into the measuring position.

An alternative to the above is proposed by claim 5. According to claim 5, a pressure medium cylinder is arranged between the coolant feed to at least one test coil, and the short leg of the "L" of a test coil support disposed opposite said test coil. The piston of said cylinder is acted upon the shorter leg of the "L" via a bypass line by means of a piston rod as soon as the pressure of the coolant has exceeded a defined pressure value, causing the test coil to be pressed from a position removed from the rolling stock and into the measuring position. In the present case, too, the leading end of the rolling stock to be measured can be excluded during the measuring process by raising the pressure of the coolant to the required value only after said leading end has passed through, so that the small pressure medium cylinder is capable of pressing the test coil into the measuring position.

The lifted-off position can, be effected by spring force in the present case as well, but also by centrifugal force.

Although it is conceivable that each test coil or each test coil support can be equipped with a device according to claim 4 or claim 5, provision is preferably made according to the claim 6 that the swinging movements of the test coil supports are synchronized with each other. Such synchronization is accomplished with methods the expert in the field is familiar with (for example steering rod gear, rack-and-pinion gear, etc.).

The invention is shown and explained in greater detail in the following with the help of drawings, in which.

Figure 1:
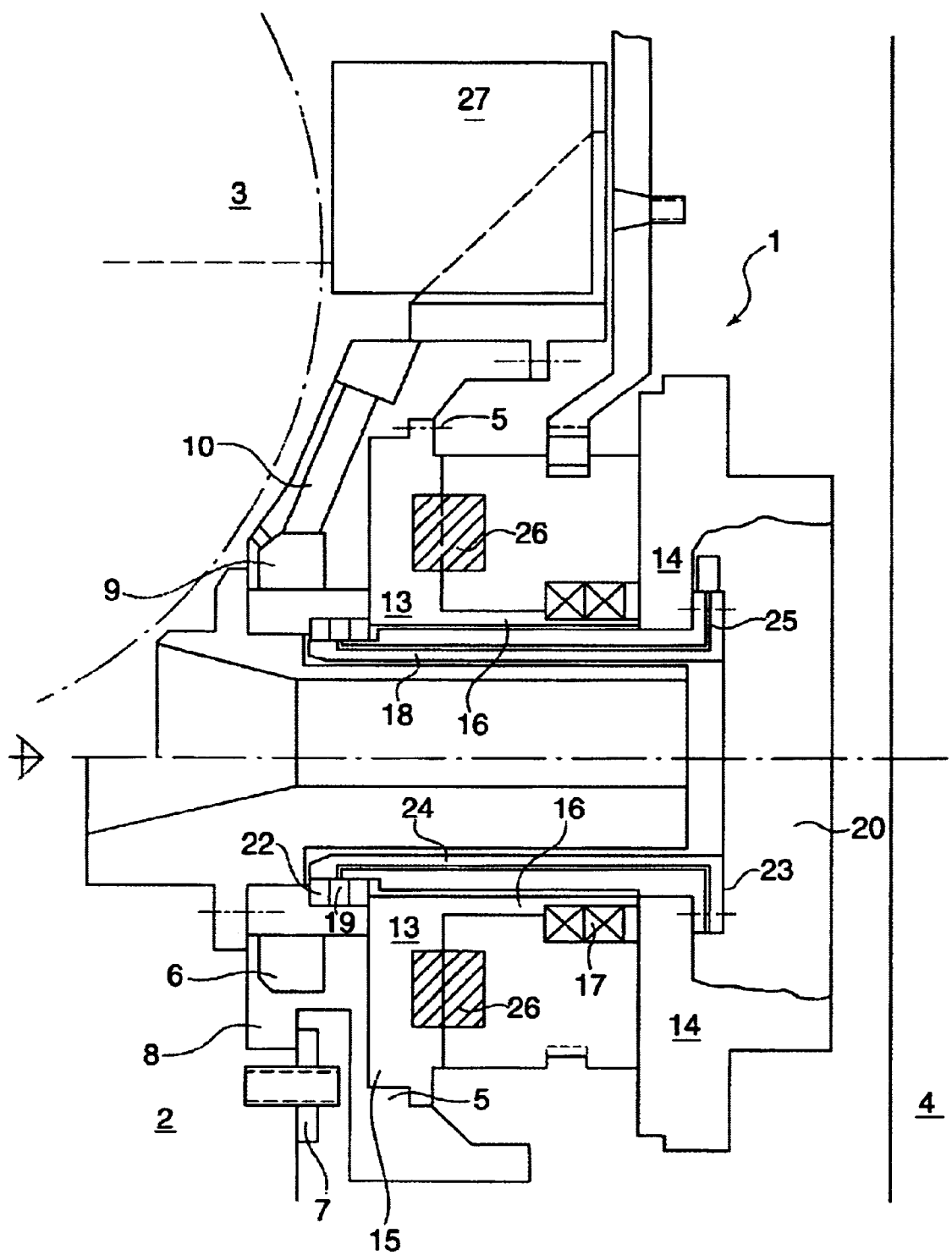
FIG. 1 shows a cross section of the rotating test coil system.
Figure 2:
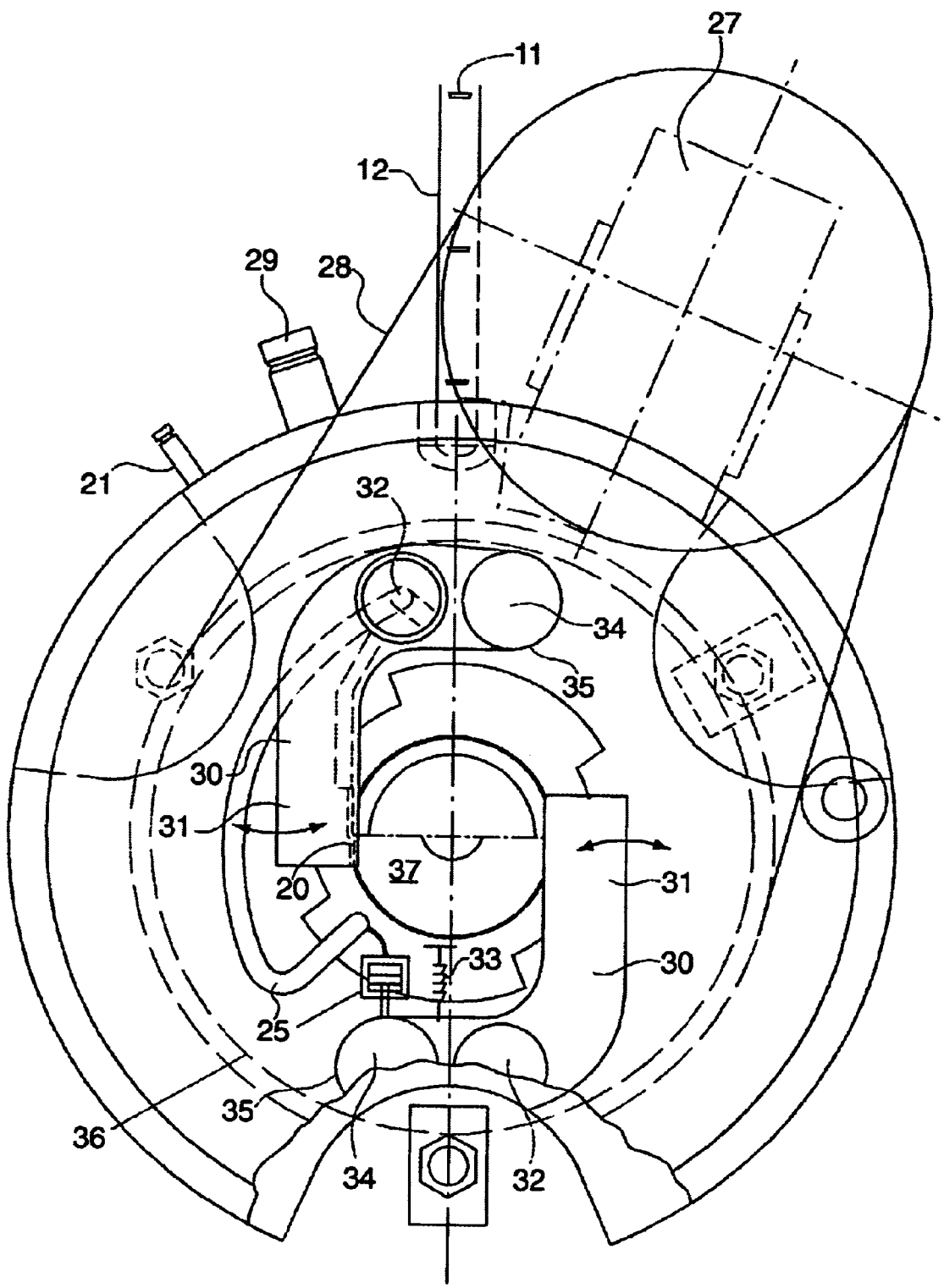
FIG. 2 shows a front view of the rotating test coil system according to FIG. 1.

FIG. 1 shows a sectional view of a device as defined by the invention, which is generally denoted by the reference numeral 1. Said device 1 is secured on a rolling stand 2. A roll 3 of said stand is indicated by dash-dotted lines. Reference numeral 4 denotes a rolling stand located downstream, which, however, is only indicated. The device 1 is secured on the roll cooling system 6 associated with the rolling stand by the screw bolts 5, which are only indicated, and said roll cooling system 6 itself is secured on the rolling stand itself with the help of the fastening means 7. The roll cooling system 6 substantially consists of a ring flange 8 serving as the housing for a ring-shaped cooling water channel 9, from which the coolant channels 10 branch off in a radial manner. As shown in FIG. 2, said coolant channels are formed by the tubes 12, which are provided with the nozzle openings 11. Said tubes 12 are directed at the surfaces of the rolls 3 to be cooled.

Such a roll cooling system is referred to also as antlers because especially in conjunction with so-called Kocks blocks, where three rolls each are offset in relation to each other by 120° and define the roll gap, three of such nozzle tubes branch off from the ring flange, with a piece of said tubes being bent around the respective periphery of the roll. The device as defined by the invention substantially comprises a stationary part and a rotating part 14. The stationary part 13 substantially consists of a ring flange 15 that is screwed to the roll cooling system 6, and a cylindrical part 16 that projects from said ring flange in the axial direction. In the present exemplified embodiment, the two rotational bearings 17 are arranged next to each other on said cylindrical part 16. The rotating part 14 of the device consists of a cylindrical part 18 which extends between the rolling stock and the cylindrical part 16 of the stationary part 13 of the device 1, said cylindrical part 18 extending against the rolling direction "R" across the stationary part 13 and into the zone of the ring flange 8. The inlet 19 for the coolant for the test coils 20, which is only indicated in FIG. 1, is located at that point. The connection 21 for said coolant inlet is shown in greater detail in FIG. 2. For sealing purposes, a gasket ring 22 is arranged between the rotating part of the device 1 and the ring flange 8 of the roll cooling system 6. A coolant channel extends from the coolant inlet 19 to the front side 23 of the rotating part of the device 1. Said coolant channel is designed in the form of a channel 24 extending around in the manner of a thread. The coolant channel 24 extending in the form of a thread changes on the front 23 of the device 1 into the individual coolant lines 25; the further extension of the latter is more clearly shown in FIG. 2.

The signals generated by the test coils 20 are transmitted via the inductive elements 26 from the rotating part of the device 1 to the stationary part of the device 1, and are further transmitted from there for evaluation.

The rotational motion of the rotating part of the device 1 is generated by means of a suitable drive, for example by means of a hydraulic motor 27, whose rotational motion is transmitted to the rotating part of the device 1 via a toothed belt 28.

FIG. 2 shows a front view of the device as defined by the invention. Identical components are denoted by the same reference numerals as those used in FIG. 1. Reference numeral 29 in FIG. 2 denotes the connection for the roll cooling system.

Said FIG. 2 shows that the test coils 20 are arranged-on the L-shaped supports 30, said supports having the shape of an angle lever. The test coils 20 are located at the end of the longer leg 31. In the present exemplified embodiment, the two test coil supports 30 are arranged point-symmetrically in relation to each other. Both test coil supports 30 have a pivot 32, in whose zone the coolant line 25 changes into the test coil support 30.

The measuring condition is shown in FIG. 2, i.e. when in the condition shown there, the test coils 20 are in the measuring position on the rolling stock to be tested, or slightly removed from the latter by 1 to 2 mm.

In order to protect the test coils against damage and to assure that the test process is started only when material is in fact passing through between the test coils, which is relevant to the measurement, the test coils are first lifted from the rolling stock. This is accomplished, for example with the help of a tension spring 33, which engages the shorter leg 34 of the "L". For the measurement, the rotational system has to have a defined rotation frequency. Said frequency is adequately high that the centrifugal force exerted on the leg 34 of the "L", said leg being provided with a counterweight 35, will become higher than the force of the spring 33, causing the longer leg 31 of the "L" with the test coil 20 to move into the measuring position.

The same drawing shows an alternative to the above embodiment. Said alternative consists in that a small pressure medium cylinder 36 is arranged between one of the coolant lines 25 and the shorter leg 34 of the "L" of a test coil support 30 that is disposed opposite the test coil support 30 which is associated with said coolant line 25. The cylinder is connected with the coolant line 25 via a bypass line 37.

The measuring process starts in this connection only once an adequate water pressure prevails in the coolant line 25, said water pressure being adequately high for causing the cooling water fed into the cylinder 36 to press the piston and thus the piston rod of the pressure medium cylinder 36 downwards against the shorter leg 34 of the support 30, which causes the longer leg 31 of the "L" with the test coil 20 to move into the measuring position as well. Synchronizing elements not shown assure that all participating test coil supports 30 are swiveling synchronously.

Figure 3:
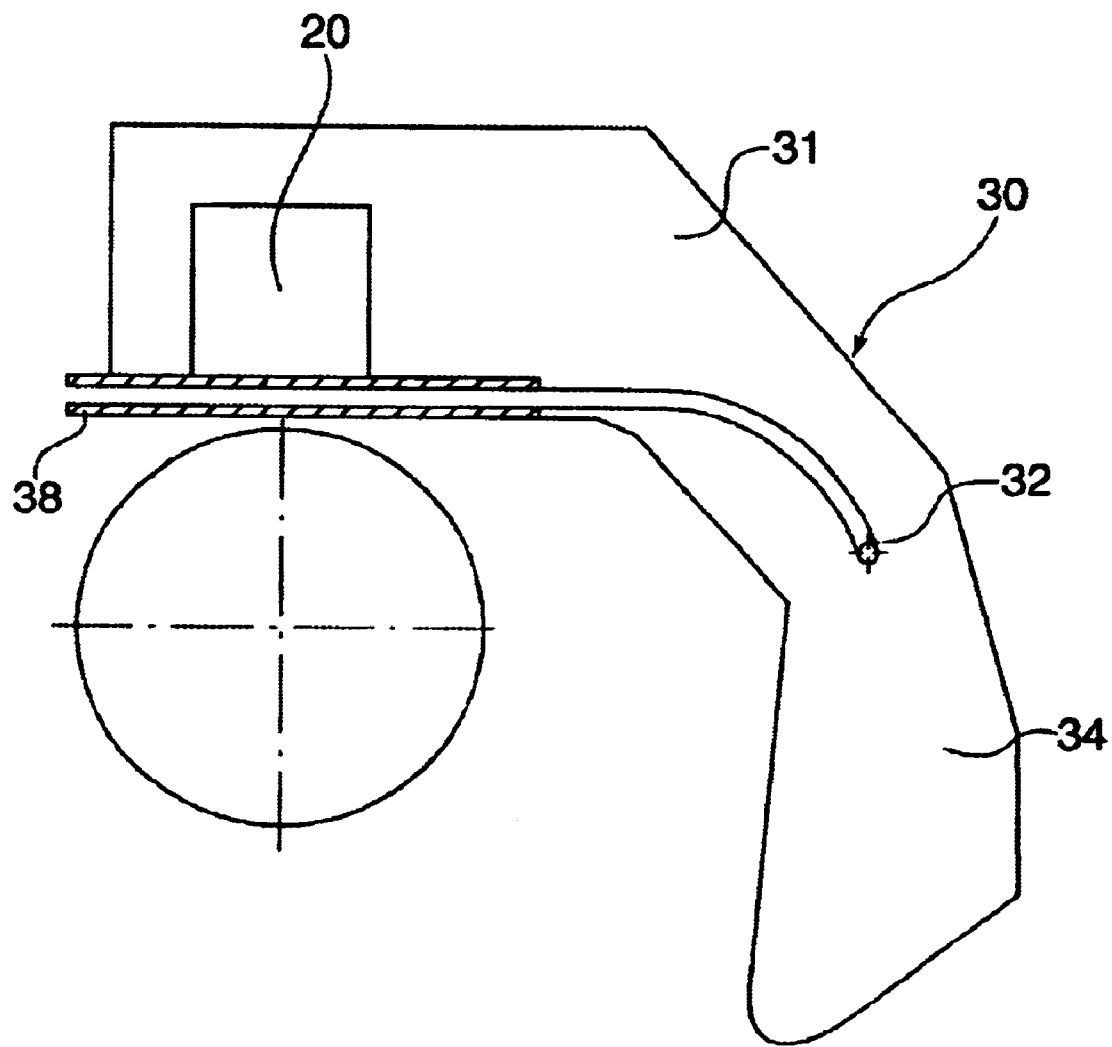
FIG. 3 shows an example of a test coil system.

FIG. 3, finally, shows by way of example how the coolant is fed to the individual test coils 20. In the present embodiment, a double-walled housing made of a ceramic material is arranged on the longer leg 31 of the "L" of the test coil support 30 in front of the test coil 20, whereby the cooling water flowing past the test coil 20 exits on the outer front side of the housing 38.

What is claimed is:

1. A device for nondestructively testing hot, bar-shaped rolling stock above the Curie point, and in the course of the rolling process from a rolling stand, the device comprising:
   a test coil system acted on by coolant and having at least two test coils, wherein each test coil is disposed on an end of a longer leg of an L-shaped support capable of swinging around an axis that extends through a zone of intersection of its legs;
   a rotating system-that rotates said test coil system and into which coolant is fed for said test coil system in the plane in which the device is secured to the rolling stand;
   a coolant channel in said rotating system that extends around in a thread-like manner to a front side of said rotating system between the rolling stock and a rotational bearing;
   individual lines that lead from said coolant channel to said test coils in a radial manner; and
   a roll cooling system coupled to the rolling stand and said rotating system, wherein the device is disposed downstream of a point where rolling stock exists from said rolling stand.

2. The device according to claim 1, wherein said rotating system flanged coaxially with said ring-shaped channel to a housing of said channel.

3. The device according to claim 1, further comprising a spring that engages one leg of said L-shaped support, wherein said spring retains said test coil in a position removed from the rolling stock until a defined rotating frequency is exceeded, whereupon said test coil is driven into a measuring position due to increased centrifugal force.

4. The device according to claim 3, wherein said swinging motions of said L-shaped supports are synchronized with each other.

5. The device according to claim 1, further comprising a pressure medium cylinder disposed between at least one of said test coils associated with said individual line, and a shorter leg of said L-shaped support disposed opposite said test coil, wherein a piston of said pressure medium cylinder, when acted upon by the coolant, acts by means of a piston rod upon said shorter leg of said L-shaped support: as soon as the pressure of the coolant has exceeded a defined value, causing said test coil to be pressed from a position removed from the rolling stock into a measuring position.

6. The device according to claim 1, wherein the device is arranged between said rolling stock outlet of the rolling stand and a rolling stock inlet of another rolling stand directly following downstream.

* * * * *